(12) United States Patent
Ihalainen

(10) Patent No.: US 7,104,689 B2
(45) Date of Patent: Sep. 12, 2006

(54) POSITIONING DEVICE AND METHOD IN X-RAY IMAGING SYSTEMS

(75) Inventor: Pekka Ihalainen, Helsinki (FI)

(73) Assignee: Instrumentarium Corporation (FI)

(*) Notice: Subject to any disclaimer, the term of this patent is extended or adjusted under 35 U.S.C. 154(b) by 255 days.

(21) Appl. No.: 10/349,506

(22) Filed: Jan. 22, 2003

(65) Prior Publication Data
US 2004/0141590 A1 Jul. 22, 2004

(51) Int. Cl.
*A61B 6/08* (2006.01)

(52) U.S. Cl. ...................................... 378/206
(58) Field of Classification Search ................... 378/206
See application file for complete search history.

(56) References Cited

U.S. PATENT DOCUMENTS

| | | | | |
|---|---|---|---|---|
| 2,376,836 A | * | 5/1945 | Tunnicliffe | 356/3.1 |
| 2,556,866 A | * | 6/1951 | Bucky | 378/98 |
| 2,659,824 A | * | 11/1953 | Burnham | 378/206 |
| 5,068,887 A | * | 11/1991 | Hughes | 378/170 |
| 5,176,689 A | * | 1/1993 | Hardy et al. | 606/130 |
| 5,359,637 A | | 10/1994 | Webber | |
| 5,657,368 A | * | 8/1997 | Rockseisen | 378/206 |
| 5,668,844 A | | 9/1997 | Webber | |
| 5,734,692 A | * | 3/1998 | Seki | 378/65 |
| 5,835,562 A | * | 11/1998 | Ramsdell et al. | 378/206 |

FOREIGN PATENT DOCUMENTS

| | | | |
|---|---|---|---|
| FR | 2648561 A1 | * | 12/1990 |
| GB | 2212040 A | * | 7/1989 |
| WO | 00/57788 | | 10/2000 |

* cited by examiner

*Primary Examiner*—Edward J. Glick
*Assistant Examiner*—Krystyna Suchecki
(74) *Attorney, Agent, or Firm*—Andrus, Sceales, Starke & Sav

(57) ABSTRACT

The invention concerns a device 5 for aiming an object 1 in an X-ray imaging apparatus 3 provided with a radiographic imaging detector 4, a radiation source 13, and transfer means for moving e.g. the radiation source into different points along a predetermined path P. Said device comprises at least one laser 6 emitting visible light, and e.g. at least two light guides having first ends and second ends, said first ends connected to said laser for receiving said visible light. Each of said second ends 8a, 8b, 8c provides a light beam, and these light beams 7a, 7b, 7c are directed towards said imaging detector with an angle of convergence K. The light beams are adjusted to intersect in a predetermined focus $F_L$ point, which is visible and indicates the proper position of the target 2 inside the object.

22 Claims, 3 Drawing Sheets

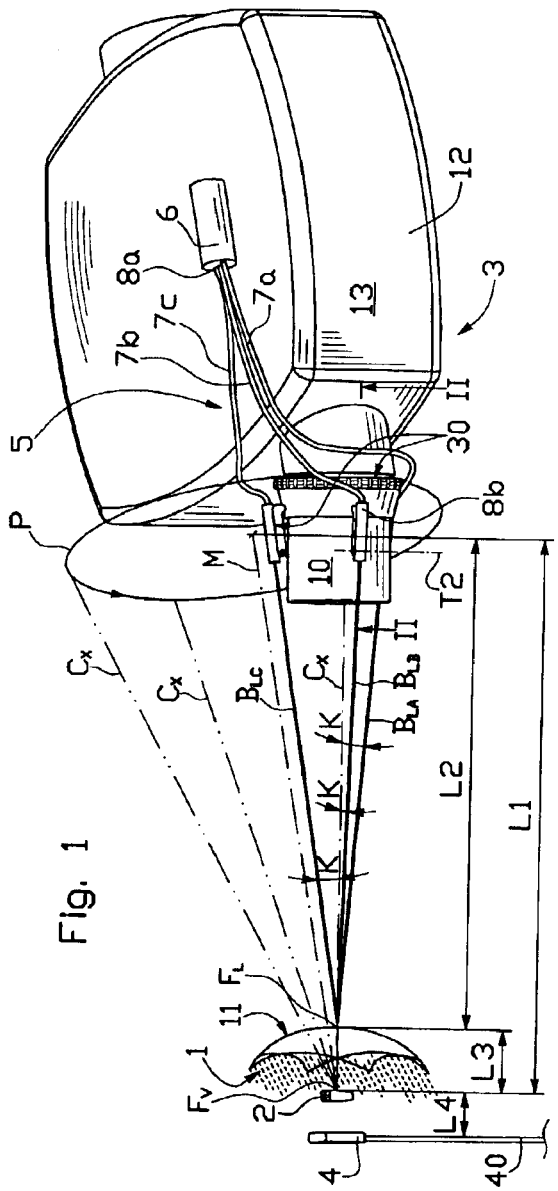
Fig. 1
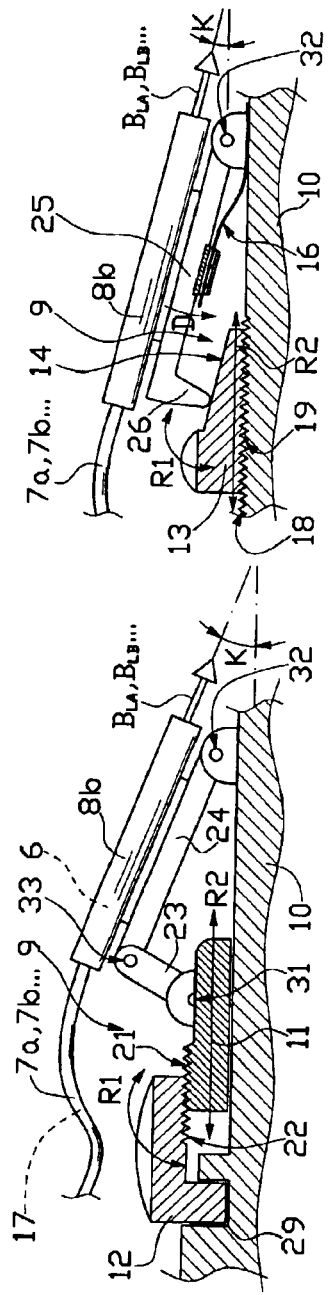
Fig. 4
Fig. 5

POSITIONING DEVICE AND METHOD IN X-RAY IMAGING SYSTEMS

FIELD OF THE INVENTION

The present invention relates to a device and a method, which aids correct positioning of an object between a radiographic imaging detector and a radiation source providing an exposing X-ray beam in X-ray imaging systems, where said radiation source moves along a predetermined path. Especially the invention is directed for attaining an optimal position of a human or animal target, like head and neck area, in a tomosynthetic X-ray system.

BACKGROUND OF THE INVENTION

Panoramic and tomographic imaging systems are widely used for attaining images from target areas of humans and animals, and nowadays these systems are also used for taking three-dimensional X-ray photographs from target volumes of humans and animals, whereupon solid-state detectors like radiation sensitive semiconductor sensor, e.g. CCD-sensors or other kind of sensor systems producing digital image data are typically utilized. The principles of the three-dimensional X-ray imaging are disclosed e.g. in U.S. Pat. Nos. 5,359,637 and 5,668,844. For three-dimensional X-ray imaging it is important that the image sensor is in correct position in respect to the X-ray source. The mutual positioning of the radiation source and the irradiation plane for the X-ray photography of the head and neck area, especially for producing three-dimensional X-ray photographs, is disclosed in publication WO-00/57788. For this purpose the imaging apparatus is equipped with an X-ray source and a digital image sensor, which is positioned in the radiation field of the X-ray source of the imaging apparatus, behind the object to be imaged each time, as viewed from the X-ray source is used. The radiation source is positioned on an irradiation plane located at a desired distance from the image sensor and the radiation source is moved on said irradiation plane along an essentially circular path in such a way that the central ray of the X-ray source is directed at the same point during the movement. The sensor is positioned at this point or in its vicinity. In order to image the object from different directions, the X-ray source is optionally stopped at the desired points of the circular path for the duration of exposure in each desired direction of imaging. The distance of the X-ray source from the sensor is measured using measuring means like measuring rod having an adjustable length, which measuring rod is located in the casing and positioned against, for example, a stopper outside the mouth which is connected to the image sensor, followed by directing the X-ray at the sensor mechanically, or by means of a ray of light, or by means of ultrasound.

The main object of the invention is to attain a method and an apparatus for pointing the predetermined position of the target, especially the predetermined distance of the target from the X-ray source. The second object of the invention is to attain such a pointing method and pointing apparatus, which does not impair under any circumstances the quality of the X-ray image. The third object of the invention is to attain such pointing method and pointing apparatus, which is accurate, easy to use and allows controlling the position of the target during X-ray imaging.

SUMMARY OF THE INVENTION

According to the first aspect of the invention it is provided a device for aiming a human or animal object in an X-ray imaging apparatus provided with: a radio-graphic imaging detector; a radiation source within a casing having radiation transparent means for output of an exposing X-ray beam to said imaging detector, said X-ray beam having a centerline; transfer means for moving said radiation source into different points along a predetermined path; and a space between said radiation source and said imaging detector for positioning said object. The first embodiment of said device comprises: at least one laser, emitting visible light; and at least two light guides having first ends and second ends, said first ends connected to said at least one laser for receiving said visible light, and each of said second ends positioned around said radiation transparent means and providing a light beam; said light beams exit from said second ends being directed towards said imaging detector with an angle of convergence between each of said light beams and said centerline of the X-ray beam, and said light beams from said second ends are adjusted to intersect in a predetermined focus point visible within said space, said focus point individually indicating a proper position of the object for an X-ray imaging thereof. The second embodiment of said device comprises: at least two lasers, emitting visible light, positioned around said radiation transparent means and providing light beams, and said light beams being directed towards said imaging detector with an angle of convergence between each of said light beams and said centerline of the X-ray beam; said light beams being adjusted to intersect in a predetermined focus point visible within said space, said focus point individually indicating a proper position of the object for an X-ray imaging thereof.

According to the second aspect of the invention it is provided a method for positioning an object in respect to an X-ray source and/or a radiographic imaging detector in a tomographic or panoramic imaging apparatus provided either with a laser emitting visible light and light guides dividing said emitted light as light beams, or with at least two lasers emitting visible light as light beams, to exit from a plurality of points by said X-ray source and directing said light beams to form a visible focus point. Said method comprises the steps of: determining a proper object distance from said X-ray source; adjusting said light beams to have said focus point thereof at said determined object distance; positioning said object between said X-ray source and said radiographic imaging detector so that said visible focus point is on said object; and performing a tomographic exposure for receiving an image of said object.

BRIEF DESCRIPTION OF THE DRAWINGS

The foregoing summary, and the following detailed description of the preferred embodiments of the present invention, will be better understood when read in conjunction with the accompanying drawings, in which:

FIG. 1 represents the first embodiment of the device according to the invention arranged in a tomographic X-ray imaging apparatus, said device employing light beams with a focus point for visualizing that range in which the body surface of a patient should be positioned so that the target further in the body of the patient is in correct place for X-ray imaging, in perspectived view.

FIG. 4 represents one possible embodiment of the adjustment means through which the angles of convergence between the visible light beams and the centerline of the X-ray beam can be altered, in a longitudinal section I—I of FIG. 3.

FIG. 5 represents another possible embodiment of the adjustment means through which the angles of convergence between the visible light beams and the centerline of the X-ray beam can be altered, in a longitudinal section II—II of FIG. 1.

DETAILED DESCRIPTION OF THE PREFERRED EMBODIMENTS

Figure 2:
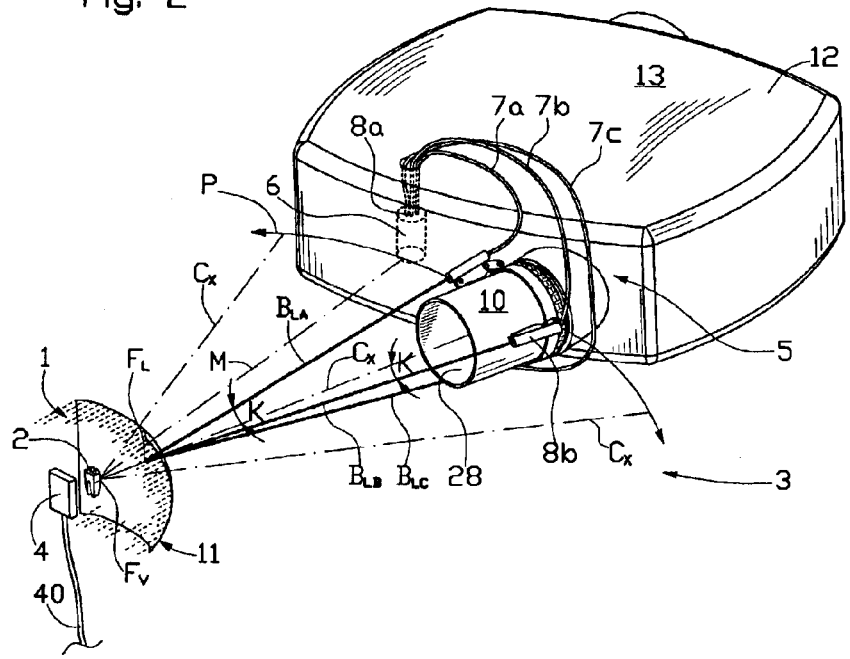
FIG. 2 represents the second embodiment of the device according to the invention arranged in a panoramic X-ray imaging apparatus, said device employing light beams with a focus point for visualizing that range in which the body surface of a patient should be positioned so that the target further in the body of the patient is in correct place for X-ray imaging, in perspectived view.
Figure 3:
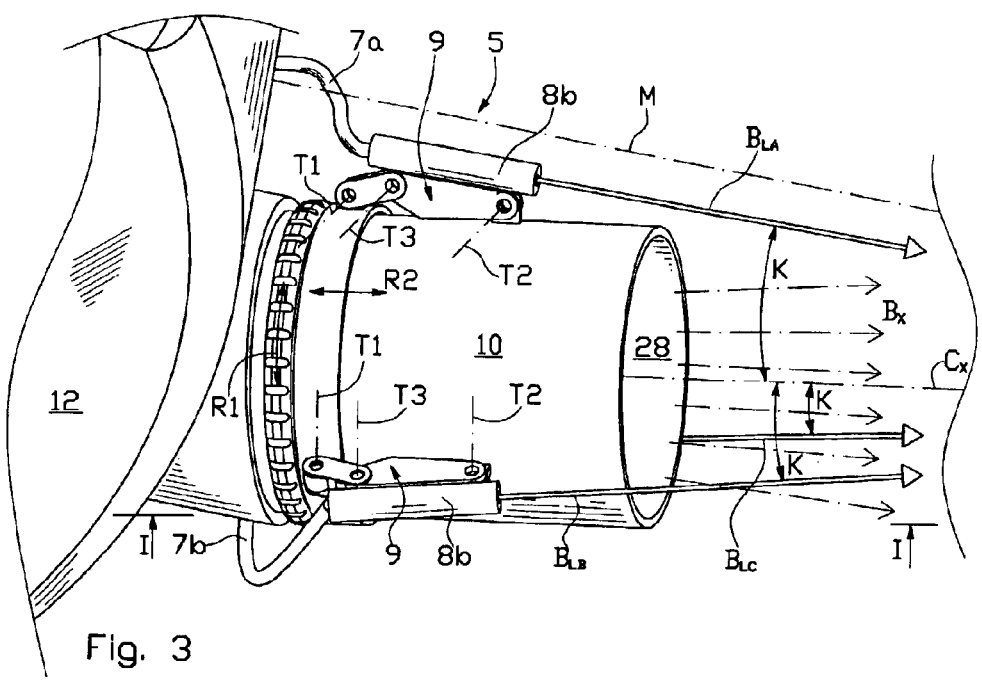
FIG. 3 represents the arrangement of the second ends of the light guides extending from a laser around the X-ray transparent means of the X-ray imaging apparatus, said second ends directed to exit the light beams so as to form a common focus point along the center axis line of the exposing X-ray beam, in perspective view.
Figure 6:
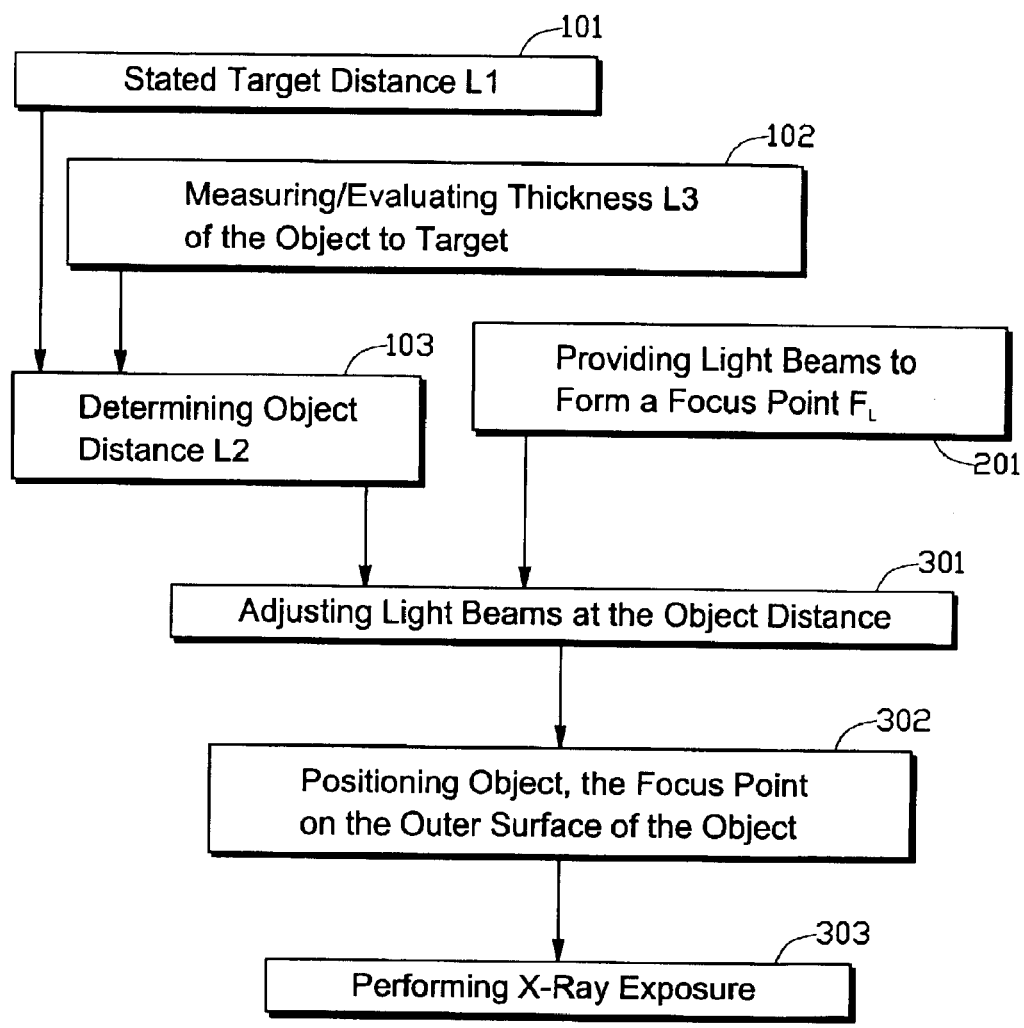
FIG. 6 is a flow chart describing the main steps of the method according to the invention utilized for each imaging task.

FIGS. 1 and 2 represent the general features of the invention. The human or animal object 1, i.e. the outer surface 11 of the human or animal body and the target 2 inside this human or animal body is shown schematically in the figures. In this case the target 2 is a tooth in the mouth of the patient and the outer surface 11 is the cheek of the patient, but it shall be understood that the target can be any portion like skeleton part or internal organ within the body of the patient, whereupon the outer surface is the respective skin area from the direction of the X-ray source. In this context the invention concerns a device 5 for aiming said human or animal object 1 in an X-ray imaging apparatus 3, which is of the type forming a three dimensional image about the target 2 onto an imaging detector 4. For this purpose at least the X-ray source 13 is moved, typically but not necessarily with an even velocity, along a predetermined path P, typically a circular path. The features of the imaging techniques for attaining a three dimensional image about a target are generally known and are accordingly not described in detail in this text. There is of course a space between said radiation source and said imaging detector for positioning said object.

The X-ray imaging apparatus 3 comprises a radiographic imaging detector 4, typically a CCD or CMOS device or any other known or new detector array sensitive to X-ray radiation and having a sensitive area. The detector 4 is connected to further instrumentation, not shown in the figures, through a signal cable 40. The X-ray imaging apparatus 3 further comprises a radiation source 13 within a casing 12, which has radiation transparent means 28 like an X-ray transparent window allowing output of an exposing X-ray beam $B_X$ to the imaging detector. The apparatus 3 has transfer means, not shown in the figures, for moving the radiation source—or also or alternatively the image detector—into different points along a predetermined path. Preferably the radiation source 13 moves uninterruptedly or continuously through successive points of the path P, but may alternatively move stepwise. The X-ray beam has a centerline $C_X$, and the predetermined path P is either a circle the plane of which is substantially perpendicular to the direction of said X-ray beam, as shown in FIG. 1, or a portion of a circle substantially parallel to the direction of said X-ray beam, as shown in FIG. 2. In both cases the X-ray beam forms a virtual focal point $F_V$ during movement of said radiation source along the path P. The embodiment of FIG. 1 is generally called a tomographic imaging system, and persons skilled in the art know that centerlines $C_X$ of the moving X-ray beam are not parallel to each other and not exactly perpendicular to the plane of the circular path P, but it is the mean axial line M of the path that is perpendicular to the plane of the circular path, which mean axial line goes through the center of the circle of movement and through the virtual focal point $F_V$, as shown in FIG. 1. The differences can be neglected from the point of view of the invention. The embodiment of FIG. 2 is generally called a panoramic imaging system, and persons skilled in the art know that centerlines $C_X$ of the moving X-ray beam are not parallel to each other, but are in the plane of the circular path P. In this case the mean axial line M of the path is one of centerlines and goes through the virtual focal point $F_V$, as shown in FIG. 1. Anyway in each successive point of the paths P the X-ray beam has a centerline, and the directions of the visible rays of light can be defined in respect to these centerlines $C_X$.

According to the invention the device 5 comprises at least one laser 6, which emits visible light, and preferably at least two light guides 7a, 7b, 7c having first ends 8a and second ends 8b, the first ends being connected to said at least one laser for receiving said visible light, and each of the second ends positioned around said radiation transparent means 28 and providing a light beam $B_{LA}$ and/or $B_{LB}$ and/or $B_{LC}$. These two light guides comprise a construction, in which a light guide with one first end is divided within its length so as to have at least two second ends 8a, 8b, too. In the embodiments of FIGS. 1 and 2, there is utilized one laser 6, which can be attached to the casing 12 outside or inside thereof. Alternatively the device can comprise at least two lasers 6, which are positioned in the respective positions as the second ends of the light guides, providing light beams $B_{LA}$ and/or $B_{LB}$ and/or $B_{LC}$, and connected through electrical cables 17 to a power source, as visualized in FIG. 4. The light beams $B_{LA}$, $B_{LB}$, $B_{LC}$ exiting from the second ends 8b are directed towards said imaging detector 4 with an angle K of convergence between each of the light beams and said centerline $C_X$ of the X-ray beam. These light beams $B_{LA}$, $B_{LB}$, $B_{LC}$ from said second ends are adjusted to intersect in a predetermined focus point $F_L$, which is closer to the X-ray source than said virtual focal point $F_V$ and is visible within the space between the X-ray source and the detector 4. The focus point $F_L$ individually indicates the proper position of the object for an X-ray imaging thereof. In the most preferred embodiment, the device is provided with one laser and at least three light guides. In another preferred embodiment, the device is provided with three lasers and no light guides. The light guides 7a, 7b, 7c are preferably optical fibers of a type useful for the purpose.

In general terms the visible focus point $F_L$ is determined to be an interspace L3 from said virtual focal point $F_V$ towards the X-ray radiation source, whereupon this interspace is respective to an individually evaluated or measured tissue thickness between the target within the human or animal object 1.

In order to change the angle K of convergence and so the object distance L2, i.e. the distance between the outer surface 11 of the object and the X-ray source 13, which object distance depends on the intended target distance L1, i.e. the stated distance between the target 2 within the object 1 and the X-ray source 13, and the thickness L3 of the tissue between the outer surface of the object and the target, the device comprises adjustment means 9 provided with tilting means 30 around said radiation transparent means. The thickness L3 of the tissue has an individual value for each patient also when the same target, e.g. teeth, are to be the object of imaging, and depends of course on the type of target and the surrounding body portion. The target distance L1 is determined during the design of the X-ray imaging apparatus 3. The second ends 8b of the light guides 7a, 7b, 7c, or the plurality of lasers respectively, are engaged in said tilting means preferably with equal distances from said centerline $C_X$ of the X-ray beam, which kind of configuration allows simple construction and operating to alter the angles K of convergence through said tilting means 30.

According to a first embodiment the adjustment means 9 comprise a stationary section 10, e.g. a tubular section, around the X-ray transparent window 28, a first adjustment ring 11 that is axially movable R2 in the direction of the centerline $C_X$ of the X-ray beam, and a second adjustment ring 12 that is rotatable R1 while staying in place it the axial direction R2. The first adjustment ring 11 has a first threaded portion 21, typically a male threaded section, and the second adjustment ring 12 has a second threaded portion 22, typically a female threaded section, engaging the first threaded portion. When the first adjustment ring is rotated R1, e.g. in a peripheral groove 29, it causes the axial movement R2 of the second adjustment ring 12. The tilting means 30 comprise a first lever 23 and a second lever 24 for each second end 8b. There is an interconnection 33 between each of the first levers 23 and the respective second levers 24, and a second connection 32 between each of the second levers 24 and the stationary section 10, as well as a first connection 31 between each of the first levers 23 and the respective first adjustment ring 11. The interconnections 33 and the connections 31, 32 having tilting axis lines T1, T2, T3 perpendicular to the centerline $C_X$, whereupon the rotary movement of the second adjustment ring causes the axial movement of the first adjustment ring, which axial movement in either direction changes the spacing between the second axis line T2 of the second connection 32 and the first axis T1 of the first connection 31 alters causing the movement of the third axis line T3 of the interconnection 33 towards or outwards from the centerline $C_X$, which in turn changes the angle K. The second ends 8b of the light guides are fixed to said second levers 24, whereupon the directions of the light beams changes together with the second levers.

According to a second embodiment the adjustment means 9 comprise a stationary section 10 that has a fourth threaded portion 18, typically a male threaded section. Here the tilting means 30 comprise a second lever 24 for each second end 8b, and second connections 32 between each of the second levers and the stationary section. Each of the second connections has a second tilting axis lines T2 perpendicular to said centerline just like above, and a free end portion 26. The tilting means also comprise spring or springs 16, loading the free end portions 26 of the second levers towards said stationary section in direction D. The tilting ring 13 has a wedge surface 14, typically a conical surface, slidably contacting the free end portions 26 of the second levers 24, and the tilting ring is further provided with a third threaded portion 19 engaging the fourth threaded portion 18, whereupon the tilting ring 13 is at least axially movable R2 in the direction of said centerline of the X-ray beam through rotation R1 thereof. The rotation R1 of the tilting ring 13 causes the axial movement of the same because of the threads, and accordingly the conical outer surface 14 either forces the free end portions 26 of the second levers outwards from the centerline $C_X$ against the spring load D or allows the spring load D to force the free end portions 26 towards the centerline $C_X$, whereupon the angle K changes. As above, the second ends 8b of the light guides are fixed to said second levers 24, whereupon the directions of the light beams changes together with the second levers.

In the tomographic or panoramic imaging method the object is positioned in respect to the X-ray source 13 and/or a radiographic imaging detector 4 of the apparatus provided with one laser or several lasers that emit visible light from a plurality of points by said X-ray source. As already mentioned there is 101 a stated target distance L1 between the target 2 within said object and the X-ray source, more specifically between the target the movement path P of said X-ray source. At first the thickness L3 between the target and an outer surface 11 said object 1 is either evaluated or measured 102, whereafter the proper object distance L2 from said X-ray source is determined 103, i.e. the object distance L2 between the X-ray source and the outer surface 11 of the is calculated, e.g. by subtracting said thickness L3 from said target distance L1. Then the light beams $B_{LA}$, $B_{LB}$ etc. are provided 201 and directed, i.e. the angles K of convergence are adjusted 301 as described earlier in this text at the predetermined object distance, and to form the visible focus point $F_L$. This adjustment is performed by altering angles K of convergence keeping them substantially equal in respect to each other. As it shall be understood it is needed at minimum two light beams to form an exact and visible focus point $F_L$, but it is preferred that the device is provided with three light beams. Also more than three light beams can be used. The imaging detector 4 is also positioned behind the target 2, in a direction away from the X-ray source, at a proper position that has a distance L4 from the target. Next the object 1 is positioned 302 between the X-ray source 13 and the radiographic imaging detector 4 so that the visible focus point $F_L$ is on said object. It is easy to detect any variation from this optimum state, because if the outer surface 11 is deviating from the focus point $F_L$ the operator can clearly see several weaker light spots on the outer surface 11, the number of which corresponds the number of light beams, contrary to one strong light spot that is visible in the aimed state, in which the focus point $F_L$ is exactly at the outer surface 11. Finally the tomographic or panoramic exposure is performed 303 for receiving an image of said target inside the object.

As already evident from the description above, the minimum number of the visible light beams is two, but it is believed that the most effective number of the beams is three, though four or five light beams can also be utilized without essential increase in costs. Theoretically there is no upper limit for the number of light beams from at least a geometrical point of view. The positioning device and method is preferably utilized for tomosynthetic X-ray imaging system providing three-dimensional images from the target.

What is claimed is:

1. A device for aiming a human or animal object when attached in an X-ray imaging apparatus provided with: a radiographic imaging detector; a radiation source within a casing having radiation transparent means for output of an exposing X-ray beam to said imaging detector, said X-ray beam having a centerline, at least said radiation source being movable into different points along a predetermined path; and a space between said radiation source and said imaging detector for positioning said object, said device comprising:
   at least one laser, emitting visible light; and
   at least two light guides having first ends and second ends, said first ends connected to said at least one laser for receiving said visible light, and each of said second ends positioned around said radiation transparent means and providing a light beam, and said light beams exiting from said second ends being directed towards said imaging detector with an angle of convergence between each of said light beams and said centerline of the X-ray beam, said light beams from said second ends adjusted to intersect in a predetermined focus point visible within said space, said focus point individually indicating a proper position of the object for an X-ray imaging thereof.

2. A device in accordance with claim 1, wherein said at least one laser is attached to said casing inside or outside thereof.

3. A device in accordance with claim 1, comprising one laser.

4. A device in accordance with claim 1, wherein said light guides are optical fibers.

5. A device in accordance with claim 5, comprising three light guides.

6. A device in accordance with claim 1, further comprising adjustment means provided with tilting means around said radiation transparent means; said second ends of the light guides being engaged in said tilting means with equal distances from said centerline of the X-ray beam; and said adjustment means being operative to alter said angles of convergence through said tilting means.

7. A device in accordance with claim 6, wherein said adjustment means comprise:
a stationary section,
a first adjustment ring axially movable in the direction of said centerline of the X-ray beam and having a first threaded portion, and
a second adjustment ring having a second threaded portion engaging said first threaded portion of the first adjustment ring and in place rotatable; and
said tilting means comprise:
first levers and second levers with interconnections therebetween, a first connection between each of the first levers and said first adjustment ring, and a second connection between each of the second levers and said stationary section, said interconnections and said connections having tilting axis lines perpendicular to said centerline; and
said second ends of the light guides being fixed to said second levers.

8. A device in accordance with claim 6, wherein said adjustment means comprise:
a stationary section; and
said tilting means comprise:
second levers with free end portions and a second connections between each of the second lever and said stationary section, said connections having a second tilting axis lines perpendicular to said centerline,
spring or springs, loading said free end portions of the second levers towards said stationary section,
a tilting ring, having a wedge surface slidably contacting said free end portions of the second lever, and being at least axially movable in the direction of said centerline of the X-ray beam; and
said second ends of the light guides being fixed to said second levers.

9. A device in accordance with claim 1, wherein said predetermined path is a circle or portion of a circle substantially perpendicular or substantially parallel to the direction of said X-ray beam, said X-ray beam forming a virtual focal point during movement of said radiation source along said path; and said focus point of the light beams is closer to the X-ray source than said virtual focal point.

10. A device in accordance with claim 9, wherein said focus point is determined to be an interspace from said virtual focal point towards the X-ray radiation source, said interspace being respective to an evaluated or measured tissue thickness between the target within the human or animal object and an outer surface of said object for attaining a tomosynthetic X-ray imaging system.

11. A device for aiming a human or animal object when attached in an X-ray imaging apparatus provided with: a radiographic imaging detector; a radiation source within a casing having radiation transparent means for output of an exposing X-ray beam to said imaging detector, said X-ray beam having a centerline, at least said radiation source being movable into different points along a predetermined path; and a space between said radiation source and said imaging detector for positioning said object, said device comprising:
at least two lasers, emitting visible light, positioned around said radiation transparent means and providing light beams,
said light beams being directed towards said imaging detector with an angle of convergence between each of said light beams and said centerline of the X-ray beam,
said light beams being adjusted to intersect in a predetermined focus point visible within said space, said focus point individually indicating a proper position of the object for an X-ray imaging thereof, and
adjustment means provided with tilting means around said radiation transparent means, said lasers being engaged in said tilting means with equal distances from said centerline of the X-ray beam, and said adjustment means being operative to alter said angles of convergence through said tilting means.

12. A device in accordance with claim 11, comprising three lasers.

13. A device in accordance with claim 11, wherein said adjustment means comprise:
a stationary section,
a first adjustment ring axially movable in the direction of said centerline of the X-ray beam and having a first threaded portion, and
a second adjustment ring having a second threaded portion engaging said first threaded portion of the first adjustment ring and in place rotatable; and
said tilting means comprise:
first levers and second levers with interconnections therebetween, a movable connection between each of the first levers and said first adjustment ring, and a stationary connection between each of the second levers and said stationary section, said interconnections and said connections having tilting axis lines perpendicular to said centerline; and
said second ends of the light guides being fixed to said second levers.

14. A device in accordance with claim 11, wherein said adjustment means comprise:
a stationary section; and
said tilting means comprise:
levers with free end portions and stationary connections between each of the levers and said stationary section, said connections having tilted axis lines perpendicular to said centerline,
spring or springs, loading said free end portions of the levers towards said stationary section, a tilting ring, having a wedge surface slidably contacting said free end portions of the levers, and being at least axially movable in the direction of said centerline of the X-ray beam; and said second ends of the light guides being fixed to said levers.

15. A device in accordance with claim 11, wherein said predetermined path is a circle or portion of a circle substantially perpendicular or substantially parallel to the direction of said X-ray beam, said X-ray beam forming a virtual focal point during movement of said radiation source along said path; and said focus point of the light beams is closer to the X-ray source than said virtual focal point.

16. A device in accordance with claim 15, wherein said focus point is determined to be an interspace from said virtual focal point towards the X-ray radiation source, said interspace being respective to an evaluated or measured tissue thickness between the target within the human or animal object and an outer surface of said object for attaining a tomosynthetic X-ray imaging system.

17. A method for positioning an object in respect to an X-ray source and/or a radiographic imaging detector in a tomographic or panoramic imaging apparatus provided with a laser emitting visible light, and light guides dividing said emitted light as light beams to exit from at least two points by said X-ray source and directing said light beams to form a visible focus point, said method comprising the steps of:

determining a proper object distance from said X-ray source;

adjusting said light beams to have said focus point thereof at said determined object distance;

positioning said object between said X-ray source and said radiographic imaging detector so that said visible focus point is on said object; and performing an X-ray exposure for receiving an image of said object.

18. A method in accordance with claim 17, wherein said step of determining comprises the substeps of:

evaluating or measuring a thickness between a target within said object and an outer surface of said object, said target forming an image onto said detector;

using a stated target distance between said target and a movement path of said X-ray source; and calculating said object distance from said thickness and said target distance.

19. A method in accordance with claim 17, wherein said step of adjusting comprises the substep of altering angles of convergence between said light beams and a centerline of the X-ray beam to be equal and forming said focus point.

20. A method in accordance with claim 17, wherein said positioning is, utilized for a tomosynthetic X-ray imaging system.

21. A method for positioning an object in respect to an X-ray source and/or a radiographic imaging detector in a tomographic or panoramic imaging apparatus provided with at least two laser emitting visible light as light beams by said X-ray source and directing said light beams to form a visible focus point, said method comprising the steps of:

evaluating or measuring a thickness between a target within said object and an outer surface of said object, said target forming an image onto said detector;

using a stated target distance between said target and a movement path of said X-ray source; and calculating an object distance from said thickness and said target distance;

adjusting said light beams to have said focus point thereof at said determined object distance;

positioning said object between said X-ray source and said radiographic imaging detector so that said visible focus point is on said object; and performing an X-ray exposure for receiving an image of said object.

22. A method in accordance with claim 21, wherein said step of adjusting comprises the substep of altering angles of convergence between said light beams and a centerline of the X-ray beam to be equal and forming said focus point.

* * * * *